United States Patent [19]
Weiser

[11] Patent Number: 5,898,945
[45] Date of Patent: May 4, 1999

[54] EAR MUFF

[75] Inventor: Abram Weiser, New York, N.Y.

[73] Assignee: Mark Bradley Levinson, Dallas, Tex.

[21] Appl. No.: 08/914,642

[22] Filed: Aug. 19, 1997

[51] Int. Cl.⁶ ..................................................... A61F 11/14
[52] U.S. Cl. ................................ 2/209; 128/864; 128/866
[58] Field of Search ........................ 2/209, 423; 128/864, 128/866

[56] References Cited

U.S. PATENT DOCUMENTS

| | | |
|---|---|---|
| 3,112,493 | 12/1963 | Greenberg . |
| 4,713,843 | 12/1987 | Duncan . |
| 4,872,219 | 10/1989 | Duncan . |
| 5,339,467 | 8/1994 | Brinkley . |

Primary Examiner—Diana L. Oleksa
Attorney, Agent, or Firm—John L. Sigalos

[57] ABSTRACT

An improved ear muff that is snappably engageable with the ear of the wearer. It includes an outer cover and an inner snappable annular actuating element form-fitted within said outer cover, the inner annular actuating element comprising a semi oval generally c-shaped closable ribbon-like member having closing projections and mating apertures to change the shape from that of a "c" to essentially that of an "o". When in the open, or "c" shape, the two ends of the ribbon which are opposed are non-parallel thus forming a truncated V-shaped space leading into the interior of the c, and the ribbon is essentially planar or partially curved. When in the closed, or "o" shape, the closing projections mate within the mating apertures thereby eliminating the truncated V-shaped space and causing the ribbon to assume or increase an arcuate shape. Provision is additionally made for optional inclusion of one or more electrical-to-audio transducers mounted within the muffs. Internal electrical connections are made between the transducers and external electrical connectors, thereby providing for audio listening pleasure.

18 Claims, 4 Drawing Sheets

EAR MUFF

BACKGROUND OF THE INVENTION

This invention relates to self attaching ear muffs, and more particularly to such muffs that include a snappable actuating member for snappably engaging the muffs with the ears of the wearer.

Snappable self-attaching ear muffs have heretofore been known, illustrative of which are those proposed in U.S. Pat. No. 3,112,493 granted to Julius Greenberg Dec. 3, 1963. Other related muffs have been set forth in U.S. Pat. No. 4,713,843 and 4,872,219 granted to Karen Duncan, and U.S. Pat. No. 5,339,467 granted to Herman E. Brinkley. Each of these appears to offer advantages over other types.

The snappable self-attaching ear muffs proposed in Greenberg Patent 3,112,493 appear particularly attractive in that they embody a snapping feature that facilitates attachment/detachment to and from the ear. Others embody symmetry about a transverse, or minor, axis, thus rendering them suitable for wearing on either ear.

While the proposals of the prior art appear to offer attractive features, there have been certain drawbacks. Thus, for example, in the Greenberg patent it is proposed that end portions of the core be pulled towards each other and maintained in tension by a flexible, inelastic tape. This requires expensive manufacturing steps and presents quality control problems in terms of uniform product performance.

BRIEF SUMMARY OF THE INVENTION

The improvement according to the invention hereof includes a core actuating member whose end portions are detachably affixed to each other by an improved geometrical configuration. In one embodiment, there are provided adjacent opposing ends, a pair of mating modified L-shaped sections one having a plurality of projections, and the other having a matching plurality of apertures adapted for receiving and retaining the projections. In two other embodiments, the modified L-shaped sections are eliminated and pairs of projections/recesses are provided in the opposing ends. In one of these two other embodiments, the projections are symmetrical about their center lines, whereas in the other added embodiment, the projections are asymmetrical. Thus, there are proposed improved actuating members whose preparation is simplified and whose retention in their actuating conditions is rendered more reliable. Also included are improved enclosures into which the core actuating members are form-fitted, thus producing combinations of improved character for facilitating comfort and insulating qualities of the muffs. As an added optional feature, provision is made for inclusion within the muffs of small audio transducers which act as earphones so that the muff wearer may enjoy the added convenience and pleasure of listening to music or other audible sounds while wearing the muffs.

OBJECTS AND FEATURES OF THE INVENTION

It is one general object of the invention to improve detachable ear muffs.

It is another object of the invention to facilitate manufacture of detachable ear muffs.

It is still another object of the invention to provide improved core snap actuators for detachable ear muffs.

It is yet another object of the invention to provide optional inclusion of audio capability within readily detachable ear muffs having snap actuators.

Accordingly, in accordance with one feature of the invention, a specially shaped annular snap actuating core element is formed, to which is attached as by sewing or otherwise affixing, the materials used to complete manufacture of ear muffs.

In accordance with still another feature of one embodiment of the invention, a modified c-shaped ribbon-like member is provided at opposing ends with complementing modified L-shaped regions that are adapted for overlapping each other, thus facilitating manufacture.

In accordance with yet another feature of the invention, one of the L-shaped regions is provided with a plurality of projections, and the other of the L-shaped regions is provided with a plurality of mating apertures, thus facilitating closure of the c-shaped ribbon-like member into the general shape of an "o" and changing the shape essentially to that of a truncated cone.

In accordance with yet another feature of the invention, in other embodiments, pairs of locking projections/apertures are provided at the opposing ends of the c-shaped ribbon-like member, thus facilitating detachable locking of the opposing ends together to complete formation of modified "o" geometry snappable partly arcuate members.

In accordance with one additional and optional feature of the invention, an audio transducer may be included within at least one (and preferably both) of each pair of the snappable ear muffs. These and other objects and features of the invention will be apparent from the following description, by way of example of preferred embodiments, with reference to the drawing.

DESCRIPTION OF A PREFERRED EMBODIMENT

Figure 1:
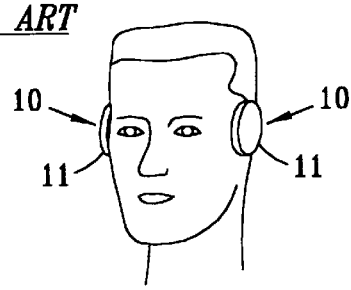
FIG. 1 is a view taken from the prior art and depicts a detachable ear muff mounted on the ear of a wearer.

Although the entirely of the foregoing U.S. Pat. No. 3,112,493 to Greenberg is herein incorporated by reference, in order to facilitate ease of understanding, a substantial part of that patent is set forth as follows:

As may be seen in FIG. 1, ear muffs 10 may be engaged with the ears of the wearer, the ear muffs 10 requiring no external band or other appliance to maintain them in the engaged position. It will be noted that the ear muffs 10 depicted in FIG. 1 are provided with an outer layer of insulating material such as fur 11 which is described hereafter in greater detail.

Figure 2:
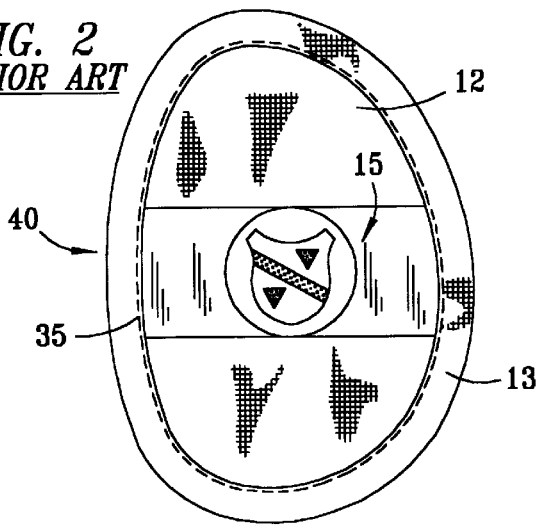
FIG. 2 is a front elevational view of a prior art detachable ear muff.
Figure 3:
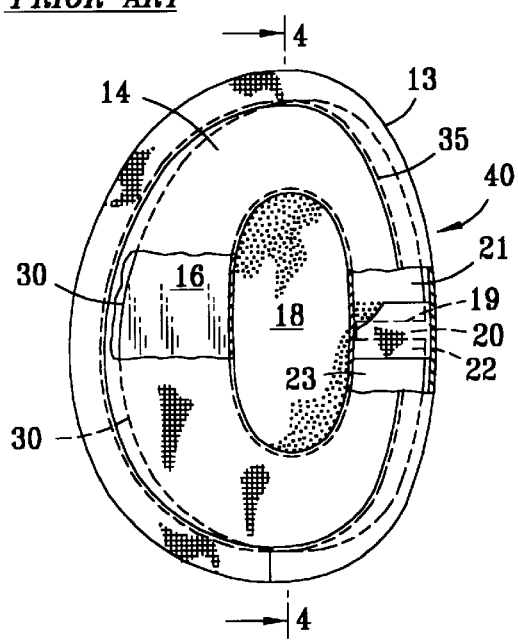
FIG. 3 is a partially cut away, rear elevational view of the embodiment of the prior art muff depicted in FIG. 2.

As depicted in FIG. 2, an outer cover 12 composed of a knitted fabric, for example, is employed in lieu of the fur 11, the cover 12 being secured as by a binding 13 to an inner face 14 (FIG. 3).

Figure 4:
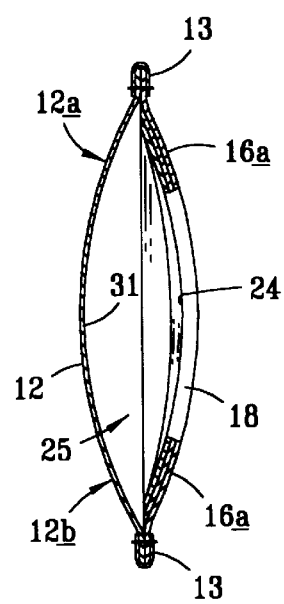
FIG. 4 is a cross-sectional view taken about the line 4—4 of FIG. 3 and depicting an open or disengaged position of the prior art muff depicted in FIGS. 2 and 3.
Figure 5:
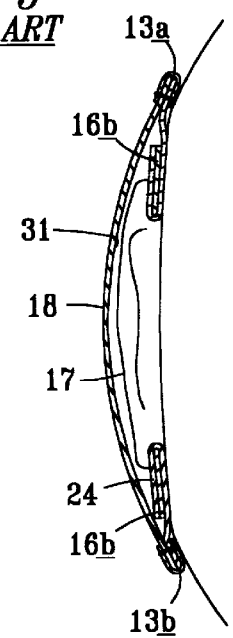
FIG. 5 is a view similar to that of FIG. 4 but depicting the prior art muff in a position wherein it is engaged with the ear of the wearer.

As may be seen in FIG. 3, the prior art muff employs a distortable core 16 which is preferably composed of a flexible, stretch-resistant plastic material. The core 16 is generally of an elongated planar conformation and is provided with a generally elliptical aperture 18 adapted to receive the ear of the wearer. The core 16 is also radially terminated as at 19 and 20 to form two end portions 21, 22 disposed in spaced relation with respect to each other. These end portions 21, 22 may be pulled toward each other and maintained in tension by a flexible, inelastic tape 23, thereby imparting a curved conformation to the core 16, as depicted in FIGS. 4 and 5, for example, where the core has assumed the curved positions designated by the numerals 16a and 16b. The inner face 14 is preferably folded around the core 16 to form a flap 24 which is secured to the inner surface of the core 16 as by a suitable adhesive.

The aperture 18 is adapted to receive the ear of the wearer so that the ear may be disposed within the area designated generally in FIG. 4 by the numeral 25. Such reception may be most easily accomplished when the ear muff is in the open position depicted in FIG. 4. However, after the ear is received in the area 25, it is necessary to exert pressure upon the upper and lower portions of the outer cover 12 as at 12a and 12b, for example, thereby urging the upper and lower ends of the ear muff toward the head of the user. Upon such urging, the core 16 will be distorted from the position depicted in FIG. 4 (the convex position) to the position depicted in FIG. 5 (the concave position), the core 16 snapping from the convex to the concave position. In the latter position, the ear muff will firmly enclose the ear lobe, and the ear lobe will bear against the inner periphery of the outer cover 12. Moreover, the upper and lower ends 13a, 13b of the ear muff will be maintained in contact with the side of the wearer's head so as to prevent access to the encased ear by wind, rain, cold and the like.

Although the outer cover 12 and the inner face 14 are united as by binding 13, they are not anchored continuously around the marginal perimeter of the inner core 16 and substantially overlap its rearward portion 30. Thus, for example, the outer cover 12, inner face 14 and inner core 16 may be united at the forward portion 40 of the muff by stitching 35 extending through the binding 13 but the stitching will unite only the outer cover 12, inner face 14 and binding 13 at the rearward portion 30 of the ear muff and will not be anchored to the inner core 16 in the vicinity of the rearward portion 30. With this arrangement, the outer cover 12 and inner face 14 are free to yieldably conform to the ear when it is received within the area 25, thereby avoiding any undesirable cramping of the ear.

To facilitate the yieldable conformation, the outer cover 12 is preferably provided with a yieldable lining 31 composed of a resilient material such as polyurethane. It will be noted also, that such a material may assume a sponge-like conformation characterized by a very soft texture and excellent heat insulation properties.

Although the outer cover 12 and inner face 14 are united by the binding 13, the inner face 14 may be composed of a plastic material which may be heat sealed at its perimeter to the plastic lining 31, thereby obviating the necessity for the binding 13.

When the ear muff is in the engaged position depicted in FIG. 5, the yieldability of the lining 31 permits the ear lobe, designated in FIG. 5 by numeral 17, to urge the outer cover 12 away from the head of the wearer without accomplishing disengagement of the ear muff from the ear lobe 17, the pressure exerted by the ear lobe 17 upon the outer cover 12 and lining 31 being insufficient to overcome the stiffness of the core 16 so as to cause the inner face 14 to be displaced from contact with the head of the wearer.

Figure 6:
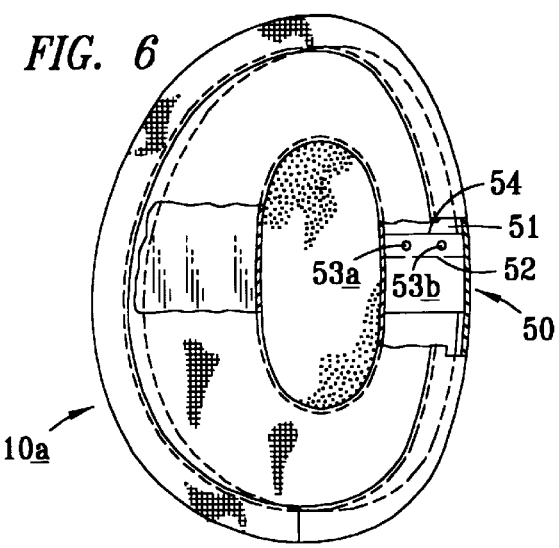
FIG. 6 is a partially cut-away view generally illustrating the muff construction according to the invention hereof.

Now turning to the remaining FIGS. 6–12 they will be seen to illustrate the inventive principles herein. FIG. 6 depicts a detachable ear muff 10a according to the invention having exterior shape generally similar to that described hereinabove with respect to FIG. 3. However, in contrast therewith FIG. 6 illustrates, as seen through cut-away portion 50, an improved core actuating ribbon-like member 51 as illustrated in greater detail in FIGS. 7–12. There are seen the member body itself in its closed, or "o"-like condition, with a joining line 52 where mating surfaces abut (as hereinafter described with respect to FIGS. 7–9B) fastening apertures 53a and 53b, and a second joining line 54. Before leaving FIG. 6, it should again be noted that core actuating member 51 is therein shown in its engaged, or "o"-like condition as illustrated in FIGS. 9A/9B.

Figure 7:
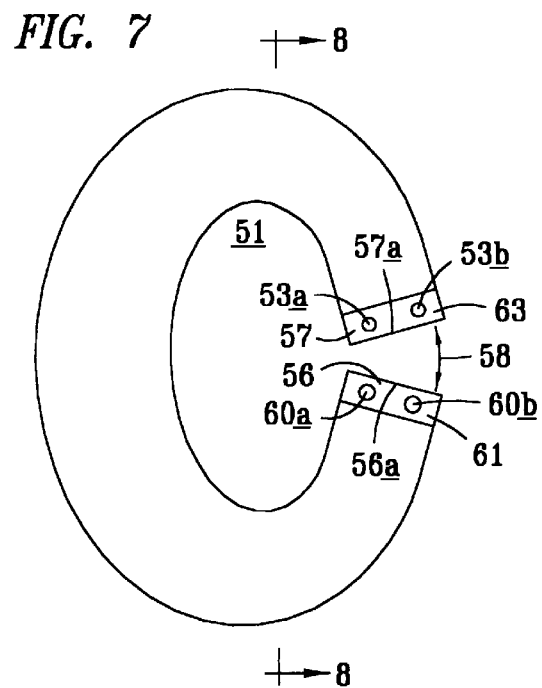
FIG. 7 is a front elevation view illustrating the generally c-shaped ribbon-like construction of a snappable actuating core according to a first embodiment of the invention.
Figure 8:
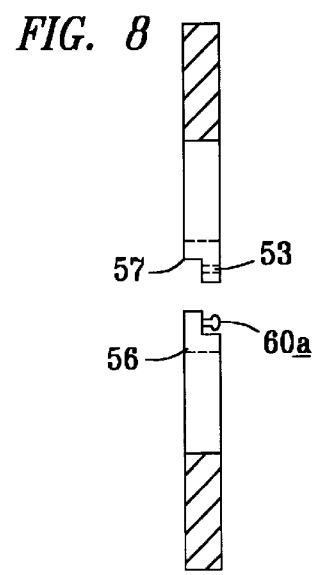
FIG. 8 is a sectional view taken along the section lines 8-8 of FIG. 7 and illustrating the planar geometry of the generally c-shaped ribbon-like core snappable actuating member of FIG. 7 before its closure into the aforementioned "o" shape.
Figure 9:
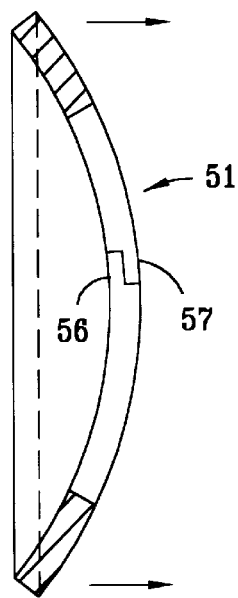
FIG. 9A is a view similar to that of FIG. 8 but illustrating the changed geometry of the ribbon-like core actuating member of FIG. 8 after closure into the aforementioned "o" shape.
FIG. 9B is a view similar to that of FIG. 9A but showing the condition of the actuating member in its other stable state as, for example, after being snapped, or toggled, into its remaining stable condition.
Figure 9:
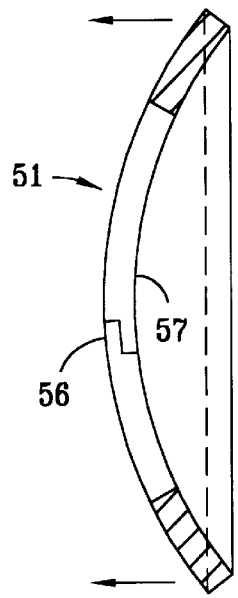

FIG. 7 is a front elevation view illustrating the ribbon-like construction of the snappable actuating core according to the first embodiment of the invention. There, in FIG. 7, the core member 51 is shown in its open, or c-shaped position in which it is essentially planar and has a cross section generally rectangular in geometry as seen in FIG. 8. It also includes a first L-shaped end 56 with a first planar end surface 56a facing a second complementing L-shaped end 57 with a second planar end surface 57a, the first planar end surface 56a and the second planar end surface 57a being in non-parallel relationship thereby to create a predetermined small non-uniform spacing 58 therebetween. As seen in FIG. 8, in addition to being L- shaped, one of the two end regions (e.g., end region 56) includes a pair of projections 60a and 60b which are either integral with or attached to the upstanding part (surface 61); and with the foregoing pair of mating apertures 53a/53b formed within the remaining (downwardly extending) L-shaped region 63. As will be observed from further reference to FIGS. 7 and 8, the projections 60a/60b and mating apertures are 53a/53b are shown therein as being in their open or disengaged condition. It will be evident that more than two projections and apertures can be utilized.

As mentioned above, FIG. 8 is a sectional view taken along the section lines 8—8 of FIG. 7 and illustrating the planar geometry of the generally c-shaped ribbon-like core snappable actuating member in its open or disengaged condition before its closure into the aforementioned "o" shape. Thus, the foregoing description of FIG. 7 is applicable to FIG. 8 as well. There, in FIG. 8, the complementary L-shapes of the ends 56 and 57 are clearly seen, together with one of the projections (i.e., projection 60a) and its mating aperture 53.

FIG. 9A is a view similar to that of FIG. 8 but illustrates the changed geometry of the ribbon-like core actuating member of FIG. 8 after closure into the aforementioned "o" shape. In the closed condition, the ends 56 and 57 are joined together and disengageably fastened by urging them toward each other with there being made sufficient displacement of end 56 with respect to end 57 so as to bring projections 60a/60b into axial alignment with mating apertures 53a/53b. Thereafter, lateral pressure is applied to extend projections 60a/60b into locking engagement with their respective apertures 53a/53b. In so doing, the previously existing small spacing 58 is, of course, eliminated, thus bowing the ribbon-like member 51 into a partly arcuate shape. This may be either the concave condition illustrated in FIG. 9A or the convex condition as illustrated in FIG. 9B. Thus, when the first end 56 is urged into planar communication with the second end 57, planar end surfaces 56a and 57a are forced into parallel relationship to eliminate the small spacing 58 and bowing the ribbon-like member.

As will be recalled from the earlier description, geometries such as those illustrated in FIGS. 9A and 9B are stable in either such condition. To proceed from one such condition to the other, end and center portions are urged in the directions shown by the arrows. When sufficient urging force is applied in the direction indicated, the core actuating member 51 snaps, or toggles, from one stable condition to the other.

Figure 10A:
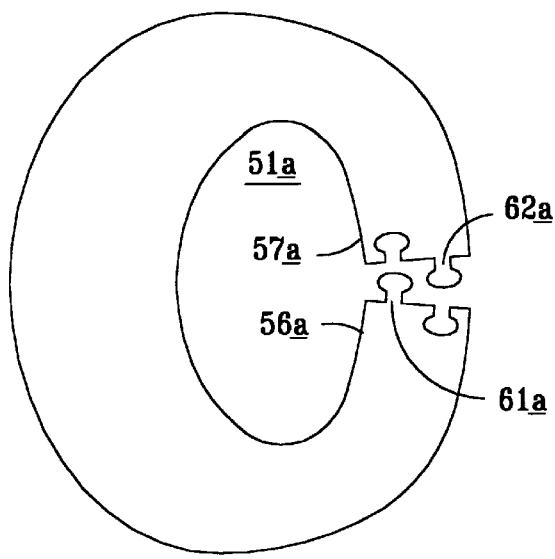
FIG. 10A is a front elevation view illustrating the generally c-shaped construction of a snappable actuating core according to a second embodiment of the invention.
Figure 10B:
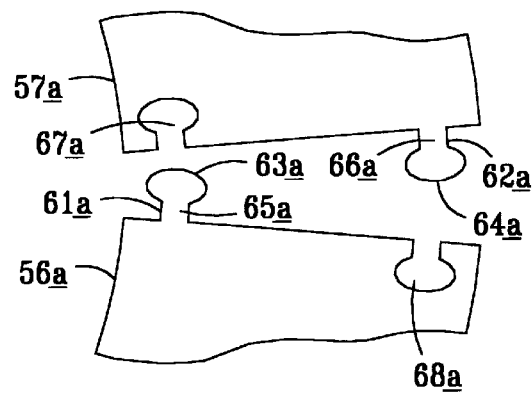
FIG. 10B is a view illustrating in detail the geometries of the engaging projections/recesses adjacent the opposing ends of the member of FIG. 10A.

Now turning to FIGS. 10A and 10B, a second embodiment of the invention is seen. There are core actuating member 51 a at whose ends 56a and 57a there are provided are pair of extending projections 61a and 62a whose extremities 63a and 64a are of greater width than their throat portions 65a and 66a (FIG. 10B) Within opposing ends, there are formed correspondingly shaped recesses 67a and 68a which are shaped to correspond to and conform in shape to mating projections 61a and 62a. Since extremities 63a and 64a are of greater width than their throat portions 65a and 66a, when the projections are urged into placed within their mating recesses, the ends 56a and 57a of member 51a are brought into and locked into engagement with each other, thus causing the member 51a to receive a bowing force thereto as was explained above in connection with the first embodiment of FIGS. 6–9B. At this point, however, and as explained below in connection with FIG. 12, the members 51a and 51b of FIGS. 10–11B are preferably constructed so as to be partially bowed even while in their disengaged or open "c" condition and thus differ from the planar construction depicted in FIG. 8. However, engagement of the ends of members 51a and 51b results in the imparting thereto an additional bowing moment which results in their achieving the intended shape corresponding generally to that of FIGS. 9A and 9B.

To achieve engagement of the ends of both the embodiments of FIGS. 10A/10B and 11A/11B, the engaging projections/recesses are urged into alignment and then pressed together so as to urge the projections into the mating recesses where they are maintained by friction therebetween unless and until it is desired to disengage them by reversing such movement. By making the members 51a/51b of slightly resilient material, and by making the projections (e.g., 61a/62a) slightly larger than the corresponding recesses 67a/68a, sufficient frictional force is obtained to secure the members in the closed and locked condition in normally encountered service within an ear muff enclosure.

Figure 11A:
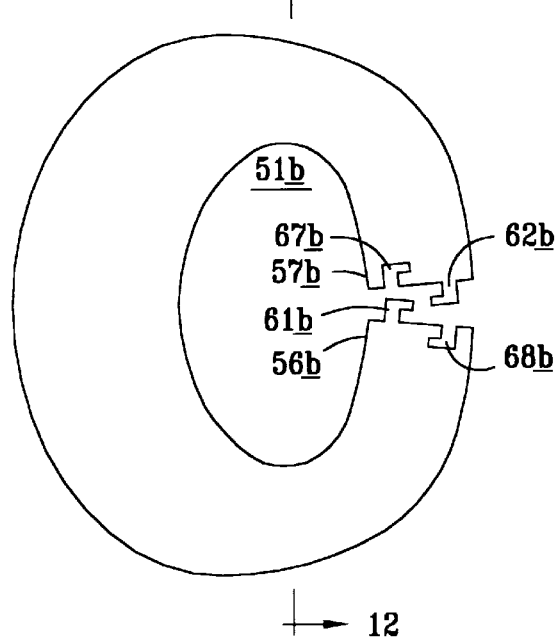
FIG. 11A is a front elevation view illustrating the snappable actuating core according to a third embodiment of the invention.
Figure 11B:
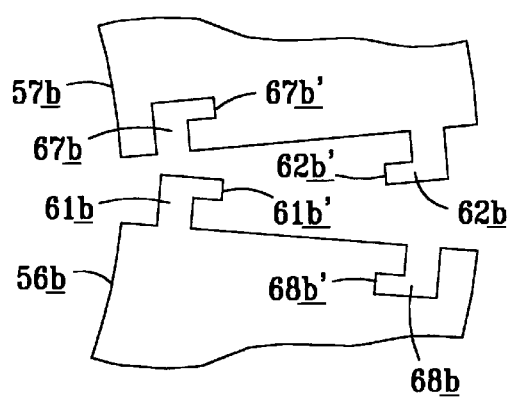
FIG. 11B is a view illustrating in detail the geometries of the engaging projections/recesses adjacent the opposing ends of the member of FIG. 11A.

FIGS. 11A and 11B depict a third embodiment of the invention which is deemed to represent the most attractive of the three embodiments herein disclosed. There, the projections 61a/62a of FIGS. 10A/10B are modified to be substantially asymmetrical about their center lines as shown in the drawing. They thus include projections/recesses that extend inwardly as denoted by numerals 61a'/62b' and 67b'/68b'. Otherwise, the foregoing description as set forth for FIGS. 10A/10B is deemed applicable to the embodiment of FIGS. 11A/11B.

Figure 12:
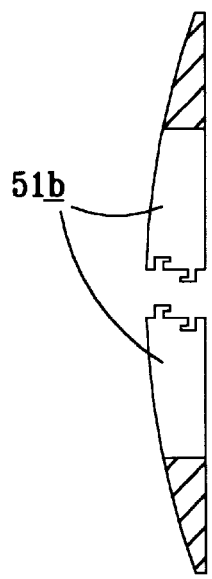
FIG. 12 is a sectional view taken along the section lines 12—12 of FIG. 11A and illustrating the curved geometry of the generally c-shaped ribbon-like core snappable actuating member of FIGS. 10A and 11A before their closures into the aforementioned "o" shapes.

To illustrate the curved, or arcuate, geometry of the members 51a and 51b, the sectional view of FIG. 12 is included. Although it is shown as being taken through member 51b of FIG. 11A, it also generally illustrates a similar section if taken through the corresponding position in FIG. 10A. There, it will be seen is the forward part of member 51b when in its disengaged, or "c" condition and depicting the initial bowing of the member according to the preferred embodiment. As previously mentioned, when the ends are locked into engagement so as to close the "c" into its "o" shape, further bowing of the member occurs according to the principles described in connection with the embodiment of FIGS. 6–9B.

Figure 13:
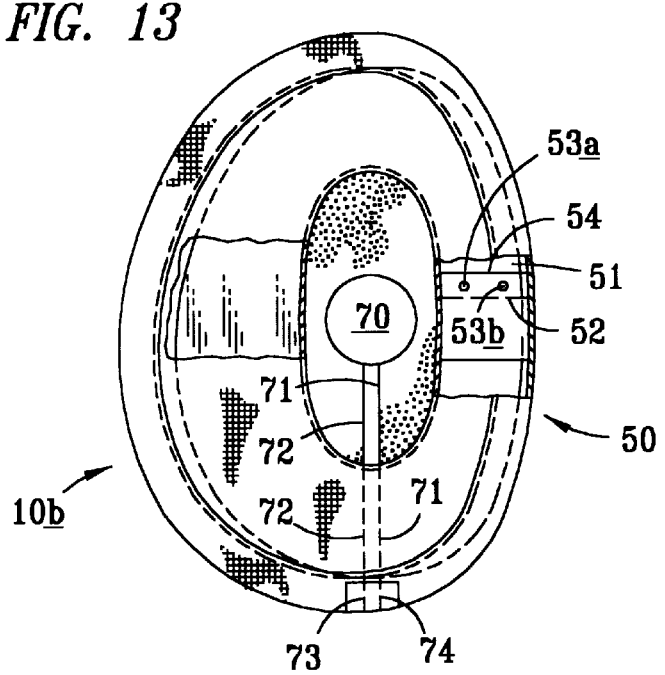
FIG. 13 is a view similar to that of FIG. 6 but including the aforementioned optional audio transducer.

Now turning to FIG. 13, there will be seen a view similar to that of FIG. 6 but including the aforementioned optional audio transducer 70 which is depicted as a circular earpiece mounted inside the muff 10b. It may be fixed in position by any of a variety of conventional fastening techniques including, for example, locating the transducer within a pocket of material, affixing it in place with adhesive, or sewing or stapling projecting tabs to an interior wall of the muff. Insulated leads 71 and 72 preferably are extended toward the exterior of the muff to conventional plug connectors 73 and 74 which may be mounted on or otherwise affixed to the muff exterior as by rivets, brads, screws and the like. By mounting the audio transducers 70 and access wiring within the muffs 10b, the problem of providing for a snug fit in the presence of a conventional earphone headband is obviated and the muffs are made much safer from leakage of cold air thereinto.

It will now be evident that there has been described herein an improved ear muff construction that facilitates manufacture and assembly thus presenting a number of advantages.

Although the invention hereof has been described by way of a preferred embodiment, it will be evident that other adaptations and modifications may be employed without departing from the spirit and scope thereof. Thus, for example, additional mating projections/recesses could be included.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. An improved ear muff comprising, in combination, an outer cover and an inner annular actuating element form-fitted within said outer cover, said inner annular actuating element comprising a semi oval generally c-shaped closable ribbon-like member, said ribbon-like member having closing means comprising projections and mating recesses, said ribbon-like member (a) when open, having a first planar end with a first end surface facing a second end with second planar end surface, said first planar end surface and said second planar end surface being in non-parallel relationship thereby to create a predetermined small non-uniform spacing therebetween, said projections being located adjacent said first end and said mating recesses being located adjacent said second end with said projections and mating recesses being disengaged; and (b) when closed, has said projections projecting into said mating recesses thereby to removably affix said ends together, said small spacing being such that when said first end is urged into contact with said second end, said first planar end surface and said second planar end surface are forced into parallel relationship eliminating said small spacing and bowing said ribbon-like member in arcuate geometry.

2. An improved ear muff according to claim 1 wherein when said ribbon-like member is closed, said complementary projections and recesses are in physical contact to disengageably lock said projections within said recesses.

3. An improved ear muff according to claim 1 wherein when said first end and said second end are disengaged, said ribbon-like member is essentially planar with a cross section generally rectangular in geometry.

4. An improved ear muff according to claim 1 wherein said first end and said second end include complementary L-shaped sections for mating engagement.

5. An improved ear muff according to claim 4 wherein when said ribbon-like member is closed, said complementary projections and recesses are in physical contact to disengageably lock said projections within said recesses.

6. An improved ear muff according to claim 4 wherein when said ribbon-like member is closed, planar regions of said complementary L-shaped sections are in physical contact.

7. An improved ear muff according to claim 1 wherein said first end and said second end partially overlap when said ribbon-like member is closed.

8. An improved ear muff according to claim 1 wherein said arcuate geometry includes a dome-shaped region.

9. An improved ear muff according to claim 1 wherein when said ribbon-like member is closed, said projections project entirely within recesses for mating and locking engagement.

10. An improved ear muff according to claim 1 wherein said first end and said second end are essentially planar in geometry.

11. An improved ear muff according to claim 1 wherein said predetermined small non-uniform spacing is substantially v-shaped.

12. An improved ear muff according to claim 1 wherein said first end and said second end partially overlap when said ribbon-like member is closed.

13. The improved ear muff according to claim 1 further including earphone means mounted within said muff, said earphone means including an electrical to audio transducer.

14. An improved ear muff according to claim 1 wherein said ribbon-like member when closed is snap actuatable between either of two different stable geometrical shapes.

15. An improved ear muff according to claim 14 wherein one of said different stable geometrical shapes is convex.

16. An improved ear muff according to claim 14 wherein one of said different stable geometrical shapes is concave.

17. An improved ear muff according to claim 14 wherein one of said two different stable geometrical shapes is convex and the other of said two different stable geometrical shapes is concave.

18. An improved ear muff comprising, in combination, an outer cover and an inner annular actuating element form-fitted within said outer cover, said inner annular actuating element comprising a semi oval generally c-shaped closable ribbon-like member, said ribbon-like member having closing means comprising projections and mating recesses, said ribbon-like member (a) when open, having a first end with a first end surface facing a second end with second end surface, said first end surface and said second end surface being in non-parallel relationship thereby to create a predetermined small substantially v-shaped spacing therebetween, said projections projecting from said first end and said mating recesses being formed within said second end with said projections and mating recesses being disengaged; and (b) when closed, said projections projecting entirely within said mating recesses thereby removably affixing said ends together, said small v-shaped spacing being such that when said first end is urged into contact with said second end, said first end and said second end are forced into engagement, thereby eliminating said small v-shaped spacing and bowing said ribbon- like member in arcuate geometry.

* * * * *